(12) United States Patent
Huang et al.

(10) Patent No.: US 11,459,361 B2
(45) Date of Patent: Oct. 4, 2022

(54) SERICIN PROTEIN PARTICLE WITH OXIDATIVE STRESS PROPERTY, METHOD FOR PREPARING THE SAME AND USE THEREOF

(71) Applicant: Hangzhou Singclean Medical Products Co., Ltd, Zhejiang (CN)

(72) Inventors: Wei Huang, Zhejiang (CN); Zhong Wang, Zhejiang (CN); Jin Zeng, Zhejiang (CN); Yurong Cai, Zhejiang (CN)

(73) Assignee: Hangzhou Singclean Medical Products Co., Ltd, Hangzhou (CN)

( * ) Notice: Subject to any disclaimer, the term of this patent is extended or adjusted under 35 U.S.C. 154(b) by 167 days.

(21) Appl. No.: 16/916,106

(22) Filed: Jun. 30, 2020

(65) Prior Publication Data
US 2021/0107954 A1    Apr. 15, 2021

(30) Foreign Application Priority Data
Oct. 11, 2019    (CN) .......................... 201910961415.8

(51) Int. Cl.
*C07K 14/435*    (2006.01)
*A61K 9/14*    (2006.01)
(52) U.S. Cl.
CPC ........ *C07K 14/43586* (2013.01); *A61K 9/146* (2013.01)
(58) Field of Classification Search
None
See application file for complete search history.

(56) References Cited

FOREIGN PATENT DOCUMENTS

| CN | 103333350 B | 5/2015 | |
|---|---|---|---|
| CN | 108186601 A | 6/2018 | |
| CN | 108478527 B | 5/2020 | |
| CN | 108186601 B | * 9/2020 | ............. A61K 47/10 |

OTHER PUBLICATIONS

English language translation of CN 108186601 B, Publ. Jun. 22, 2018. (Year: 2018).*

* cited by examiner

*Primary Examiner* — Dominic Lazaro

(57) ABSTRACT

The application relates to a sericin protein particle with an oxidative stress property, a method for preparing the same and use thereof. The particle is formed by sericin protein and a tellurium compound. In the method for preparing the sericin protein particle, bis(1-hydroxydodecyl) telluride is first prepared and then mixed with a solution of sericin protein, and a resulting solution is agitated continuously for some time to obtain telluride-modified sericin protein. Then, the solution of the sericin protein is added dropwise into absolute ethanol to obtain a precipitated product. An aqueous solution of the precipitated product and a solution of magnesium ions are mixed and agitated for a certain time to obtain the sericin protein particle with an oxidative stress property. The sericin protein particle disclosed is a hollow particle having a diameter in a range of 600-1250 nm, and is capable of loading biomacromolecule drugs or other components.

4 Claims, 2 Drawing Sheets

SERICIN PROTEIN PARTICLE WITH OXIDATIVE STRESS PROPERTY, METHOD FOR PREPARING THE SAME AND USE THEREOF

CROSS REFERENCE TO RELATED APPLICATIONS

The present application claims the benefit of Chinese Patent Application No. 201910961415.8 filed on Oct. 11, 2019, the contents of which are incorporated herein by reference in their entirety.

FIELD OF THE INVENTION

The present disclosure relates to a sericin protein particle with an oxidative stress property and a method for preparing the same, and the prepared sericin protein particle can be used as a carrier for sustained release of drugs. The present disclosure belongs to the field of biomedical materials.

BACKGROUND OF THE INVENTION

Silk is composed of silk fibroin and sericin protein. Sericin protein is a kind of globulin, accounts for about 20% to 30% of the total weight of the silk, and plays a role of binding and protecting silk fibroin in the silk. In the process of silk reeling and silk spinning, sericin is often removed completely and discharged as a by-product along with waste water. According to statistics, about 50,000 tons of sericin protein is disposed as waste every year, which leads to not only a huge waste of natural material resources but also environmental pollution. Therefore, how to develop a new type of functionalized application of this natural material while reducing pressure of sericin-containing wastewater on the natural environment is a problem that people are very concerned about.

Sericin protein has good water solubility, biocompatibility, and cell adhesion as an anti-tumor active agent. These properties lay the foundation for its application in the field of biomedical materials. For example, in Chinese patent document (ZL201310228079.9) titled "Method for preparing sericin particle", sericin particles having high embedding efficiency was obtained by: using sericin protein obtained by degumming outer floss of a cocoon as a raw material, mixing sericin protein with a drug in an aqueous solution, spraying a resulting solution at −20 to −80° C. to obtain ice particles, keeping the ice particles for four hours, and then unfreezing the ice particles. In Chinese patent document (CN 201810044872.6) titled "Sericin protein microcapsules and one-step-process preparation method", sericin protein microcapsules were obtained by: mixing sericin protein powder with 1,3-butanediol, keeping a resulting solution for 15-120 min at 120° C. under an agitating condition, and then washing the solution with water; and the sericin protein microcapsules are intended for use in fields of drug carriers, targeted delivery and skin care. In Chinese patent document (CN 201810353345.3) titled "Preparation method and use of sericin protein and polyglutamic acid self-assembled nano-micelle", sericin protein and polyglutamic acid self-assembled bodies were prepared by an electrostatic assembling method, and are intended for use in embedding of anti-cancer drugs and hydrophobic drugs. Up to now, most of the work on sericin protein used as a drug carrier has been focused on construction of different physical forms of sericin protein, and a relevant technology that enables sericin protein to have an oxidative stress property by modifying sericin protein has not yet appeared.

A drug carrier having a stimuli-responsive property, is capable of changing physically or chemically in response to specific stimuli and releasing an embedded drug to achieve responsive controllable release of the drug, and thus has attractive prospects in the field of biomedical materials. A drug carrier having an oxidative stress property is one type of drug carriers having a stimuli-responsive property. Active oxygen widely present in a living body includes hydrogen peroxide, peroxynitrite, hydroxyl radical and so on, which play an important role in processes of cell growth, apoptosis, migration and so on. However, at some lesions, active oxygen is usually present at a relatively high concentration, which may cause damage to protein, lipid and DNA. Therefore, by developing a material that is responsive to active oxygen, targeted delivery and treatment to such lesions and thus an effect of protecting a body can be realized. However, this synthesis process is long, and involves using of organic solvents for many times, which is not conducive to loading and encapsulation of water-soluble and sensitive drugs.

SUMMARY OF THE INVENTION

A first objective of the present disclosure is to overcome the above deficiencies in existing technologies and provide a method for preparing a sericin protein particle with an oxidative stress property. The preparation process of the present disclosure is simple and environmentally friendly; and obtained particles have an excellent environment-responsive property, and thus have potential application prospects in the biomedical field.

In order to realize the above objective, the technical solution of the present disclosure adopts the following steps.

The present disclosure provides a method for preparing a sericin protein particle with an oxidative stress property. The method includes the following steps of:

1) adding sodium borohydride and tellurium powder into water, heating a resulting solution to a temperature suitable for a reaction under a condition of nitrogen protection, and performing the reaction to obtain a $Na_2Te_2$ aqueous solution; cooling the $Na_2Te_2$ aqueous solution to room temperature, adding 10-bromo-dodecyl alcohol and an organic solvent thereto, heating a resulting solution to a temperature suitable for a reaction; performing the reaction, and then performing post-treatment, after the reaction is over, to obtain a white solid powder of bis(1-hydroxydodecyl) telluride;

2) preparing a telluride solution of the obtained white solid powder of bis(1-hydroxydodecyl) telluride;

3) mixing the telluride solution prepared in step 2) with a solution of sericin protein uniformly, and adding a resulting solution dropwise into absolute ethanol for a reaction to obtain a white precipitate, the obtained precipitate being telluride-modified sericin protein; and 4) preparing an aqueous solution of the telluride-modified sericin protein and an aqueous solution of magnesium ions respectively, and mixing the two solutions uniformly to obtain a mixed solution; adjusting a system of the mixed solution with HCl and NaOH to have a pH value of 5.0-8.0, then performing a reaction at a temperature suitable for the reaction and under a condition of agitating, and separating, after the reaction is over, a resulting precipitate to obtain sericin protein particles with an oxidative stress property.

A temperature for the reaction to obtain the $Na_2Te_2$ aqueous solution in step 1) is preferably 80° C. The organic solvent in step 1) is preferably tetrahydrofuran. A temperature for the reaction to obtain bis(1-hydroxydodecyl) telluride is preferably 50° C. The post-treatment in step 1) is preferably as follows: cooling a resulting reaction solution to room temperature, extracting a product by using dichloromethane, collecting a dichloromethane phase, adding excess anhydrous magnesium sulfate for drying, and subjecting a resulting solution to filtration and rotary evaporation to obtain the white solid powder of bis(1-hydroxydodecyl) telluride.

In step 2), the obtained white solid powder of bis(1-hydroxydodecyl) telluride is dissolved in N,N-dimethylformamide to prepare a telluride solution having a mass concentration of 0.2-2%.

The aqueous solution of sericin protein is prepared by dissolving sericin protein in deionized water, so that the aqueous solution of sericin protein has a mass concentration of 0.2-2%.

The prepared telluride solution and the prepared aqueous solution of sericin protein are preferably mixed at a volume ratio of 0.2-1:1.

In step 3), a temperature for the reaction is preferably 40° C., and the reaction is performed under a condition of agitating at a revolving speed of 100-500 rpm.

In step 4), a reaction solution with the pH value thereof having been adjusted is placed into a thermostat at a temperature of 30-50° C. for a reaction under a condition of agitating at a revolving speed of 100-500 rpm, and after the reaction is over, produced precipitate is separated by centrifugation.

A molecular weight distribution of the sericin protein is preferably 5-50 KDa, and the sericin protein may be obtained from silkworm silk, tussah silk, and/or other wild silk.

After the aqueous solution of the telluride-modified sericin protein and the aqueous solution of the magnesium ions are mixed, a mass percentage concentration of the sericin protein is 0.05-2%, and a concentration of the magnesium ions was 5-15 mmol/L.

The magnesium ions may be selected from any of magnesium chloride, magnesium nitrate and magnesium sulfate.

A second objective of the present disclosure is to provide a sericin protein particle with an oxidative stress property, which is prepared by using any of the above methods.

The sericin protein particle is a hollow spherical particle. A diameter of the particle is related to the concentration of the magnesium ions and a speed of agitating during synthesis, and a particle diameter distribution of the particle is in a range of 600-1250 nm.

To sum up, the present disclosure provides use of sericin protein in preparing a sericin protein particle with an oxidative stress property. The sericin protein is modified by telluride.

The present disclosure has the following beneficial effects. According to the present disclosure, after telluride-modified sericin protein is prepared, reactions are all performed in an aqueous solution under mild reaction conditions in the subsequent process of forming the sericin protein particle, which reduces pollution to the environment caused by using organic solvents, and thus the sericin protein particle can be used for loading and encapsulation of water-soluble and sensitive drugs. Moreover, a diameter of the particle may be adjusted by adjusting external conditions such as a concentration of a solution of sericin protein in a system, a concentration of a solution of metal ions, and a pH value, so as to meet different application requirements. The prepared sericin protein particle has an excellent oxidative stress stimuli-responsive property, and has wide application prospects in fields of drug carriers, targeted delivery and so on.

DETAILED DESCRIPTION OF THE EMBODIMENTS

Figure 1:
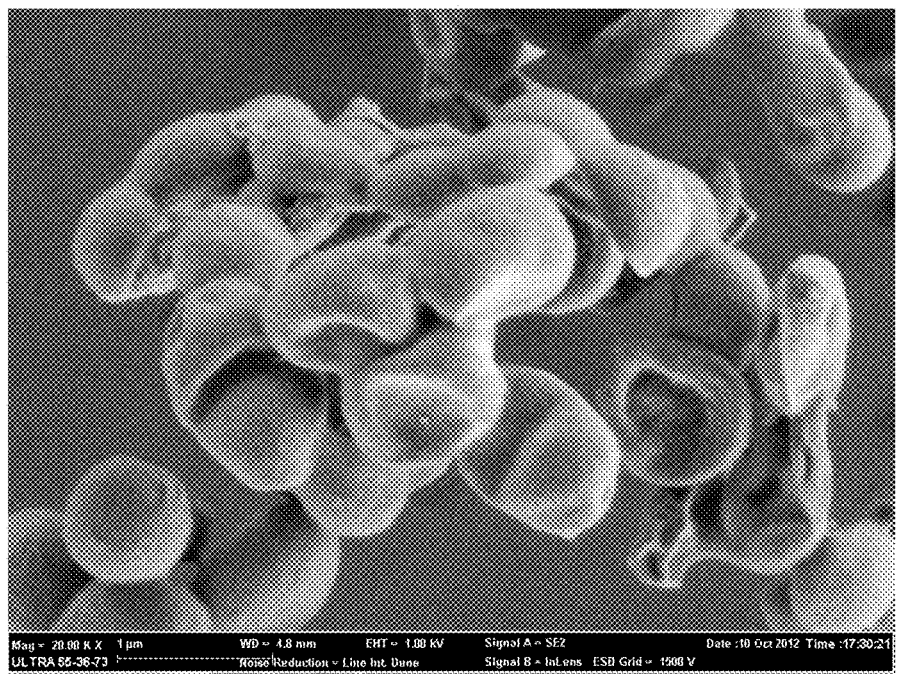
FIG. 1 is an SEM image of telluride-modified sericin particles prepared in Example 3.

The present disclosure will be further explained in conjunction with specific embodiments.

Example 1

1) 1.51 g of sodium borohydride and 4.84 g tellurium powder were added into 100 mL of water, and a resulting solution was heated to 80° C. under a condition of nitrogen protection to perform a reaction for 2.5 h to obtain a $Na_2Te_2$ aqueous solution. The $Na_2Te_2$ aqueous solution was cooled to room temperature, and 5.56 g of 10-bromo-dodecyl alcohol and 100 mL of tetrahydrofuran were added; and a resulting solution was heated to 50° C. to perform a reaction for 6 h. After the reaction was over, a resulting solution was cooled to room temperature, and a product was extracted by using dichloromethane. Then a dichloromethane phase was collected, and excess anhydrous magnesium sulfate was added for drying for 24 h; and a resulting solution was subjected to filtration and rotary evaporation to obtain a white solid powder of bis(1-hydroxydodecyl) telluride.

2) The obtained white solid powder of bis(1-hydroxydodecyl) telluride was dissolved in N,N-dimethylformamide to prepare a telluride solution having a mass concentration of 0.2%.

3) Sericin protein having a molecular weight of 5 KDa was dissolved in deionized water to prepare an aqueous solution of sericin protein with a mass concentration of 0.2%.

4) The telluride solution prepared in step 2) and the solution of sericin protein prepared in step 3) were mixed at a volume ratio of 0.2:1, and a resulting solution was agitated for 4 h at 40° C. at a revolving speed of 100 rpm. Then, the solution was added dropwise into absolute ethanol to obtain a white precipitate. The precipitate was separated by centrifugation, and the obtained precipitate was telluride-modified sericin protein.

5) An aqueous solution of the telluride-modified sericin protein and an aqueous solution of magnesium chloride were prepared respectively, and the two solutions were mixed uniformly to obtain a mixed solution, in which a mass percentage concentration of the sericin protein was 0.05%, and a concentration of magnesium ions was 5 mmol/L. After a system of the solution was adjusted with HCl and NaOH to have a pH value of 5.0, the solution was placed into a thermostat at a temperature of 30° C. to perform a reaction, during which the solution was agitated continuously for 2 h at a resolving speed of 300 rpm. Resulting precipitate was separated by centrifugation. The obtained precipitate was sericin protein particles with an oxidative stress property. An average diameter of the sericin protein particles was 1250 nm.

Example 2

1) 1.51 g of sodium borohydride and 4.84 g tellurium powder were added into 100 mL of water, and a resulting solution was heated to 80° C. under a condition of nitrogen protection to perform a reaction for 2.5 h to obtain a $Na_2Te_2$ aqueous solution. The $Na_2Te_2$ aqueous solution was cooled to room temperature, and 5.56 g of 10-bromo-dodecyl alcohol and 100 mL of tetrahydrofuran were added; and a resulting solution was heated to 50° C. to perform a reaction for 6 h. After the reaction was over, a resulting solution was cooled to room temperature, and a product was extracted by using dichloromethane. Then a dichloromethane phase was collected, and excess anhydrous magnesium sulfate was added for drying for 24 h; and a resulting solution was subjected to filtration and rotary evaporation to obtain a white solid powder of bis(1-hydroxydodecyl) telluride.

2) The obtained white solid powder of bis(1-hydroxydodecyl) telluride was dissolved in N,N-dimethylformamide to prepare a telluride solution having a mass concentration of 0.8%.

3) Sericin protein having a molecular weight of 10 KDa was dissolved in deionized water to prepare an aqueous solution of sericin protein with a mass concentration of 0.8%.

4) The telluride solution prepared in step 2) and the solution of sericin protein prepared in step 3) were mixed at a volume ratio of 0.4:1, and a resulting solution was agitated for 6 h at 40° C. at a revolving speed of 200 rpm. Then, the solution was added dropwise into absolute ethanol to obtain a white precipitate. The precipitate was separated by centrifugation, and the obtained precipitate was telluride-modified sericin protein.

5) An aqueous solution of the telluride-modified sericin protein and an aqueous solution of magnesium nitrate were prepared respectively, and the two solutions were mixed uniformly to obtain a mixed solution, in which a mass percentage concentration of the sericin protein was 0.2%, and a concentration of magnesium ions was 10 mmol/L. After a system of the solution was adjusted with HCl and NaOH to have a pH value of 6.0, the solution was placed into a thermostat at a temperature of 40° C. to perform a reaction, during which the solution was agitated continuously for 8 h at a resolving speed of 300 rpm. Resulting precipitate was separated by centrifugation. The obtained precipitate was sericin protein particles with an oxidative stress property. An average diameter of the sericin protein particles was 1080 nm.

Example 3

1) 1.51 g of sodium borohydride and 4.84 g tellurium powder were added into 100 mL of water, and a resulting solution was heated to 80° C. under a condition of nitrogen protection to perform a reaction for 2.5 h to obtain a $Na_2Te_2$ aqueous solution. The $Na_2Te_2$ aqueous solution was cooled to room temperature, and 5.56 g of 10-bromo-dodecyl alcohol and 100 mL of tetrahydrofuran were added; and a resulting solution was heated to 50° C. to perform a reaction for 6 h. After the reaction was over, a resulting solution was cooled to room temperature, and a product was extracted by using dichloromethane. Then a dichloromethane phase was collected, and excess anhydrous magnesium sulfate was added for drying for 24 h; and a resulting solution was subjected to filtration and rotary evaporation to obtain a white solid powder of bis(1-hydroxydodecyl) telluride.

2) The obtained white solid powder of bis(1-hydroxydodecyl) telluride was dissolved in N,N-dimethylformamide to prepare a telluride solution having a mass concentration of 1.5%.

3) Sericin protein having a molecular weight of 20 KDa was dissolved in deionized water to prepare an aqueous solution of sericin protein with a mass concentration of 1.5%.

4) The telluride solution prepared in step 2) and the solution of sericin protein prepared in step 3) were mixed at a volume ratio of 0.5:1, and a resulting solution was agitated for 6 h at 40° C. at a revolving speed of 200 rpm. Then, the solution was added dropwise into absolute ethanol to obtain a white precipitate. The precipitate was separated by centrifugation, and the obtained precipitate was telluride-modified sericin protein.

5) An aqueous solution of the telluride-modified sericin protein and an aqueous solution of magnesium sulfate were prepared respectively, and the two solutions were mixed uniformly to obtain a mixed solution, in which a mass percentage concentration of the sericin protein was 1%, and a concentration of magnesium ions was 10 mmol/L. After a system of the solution was adjusted with HCl and NaOH to have a pH value of 7.0, the solution was placed into a thermostat at a temperature of 40° C. to perform a reaction, during which the solution was agitated continuously for 10 h at a resolving speed of 300 rpm. Resulting precipitate was separated by centrifugation. The obtained precipitate was sericin protein particles C with an oxidative stress property. An average diameter of the sericin protein particles was 1000 nm.

Figure 2:
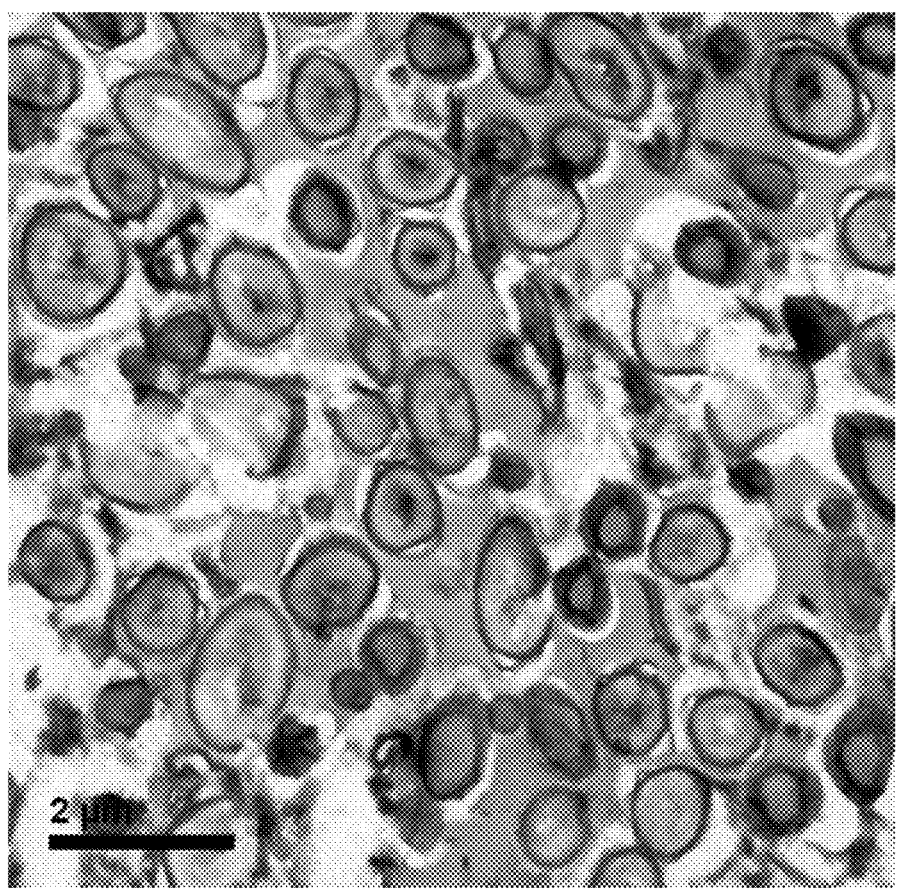
FIG. 2 is a TEM transmission slice image of the telluride-modified sericin particles prepared in Example 3.
Figure 3:
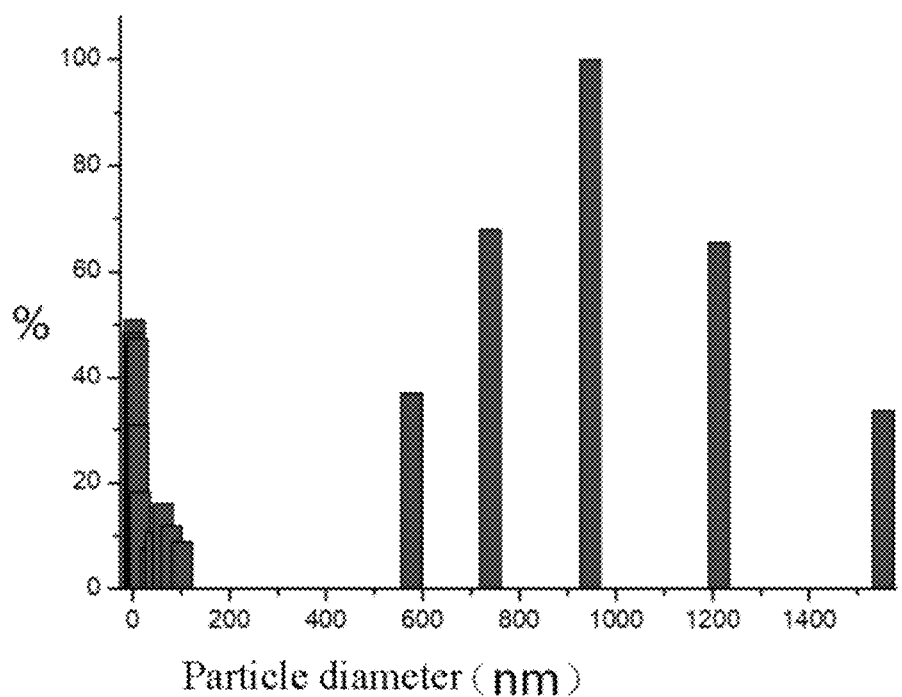
FIG. 3 is a DLS diagram showing particle diameter distribution of the telluride-modified sericin particles prepared in Example 3.
Figure 4:
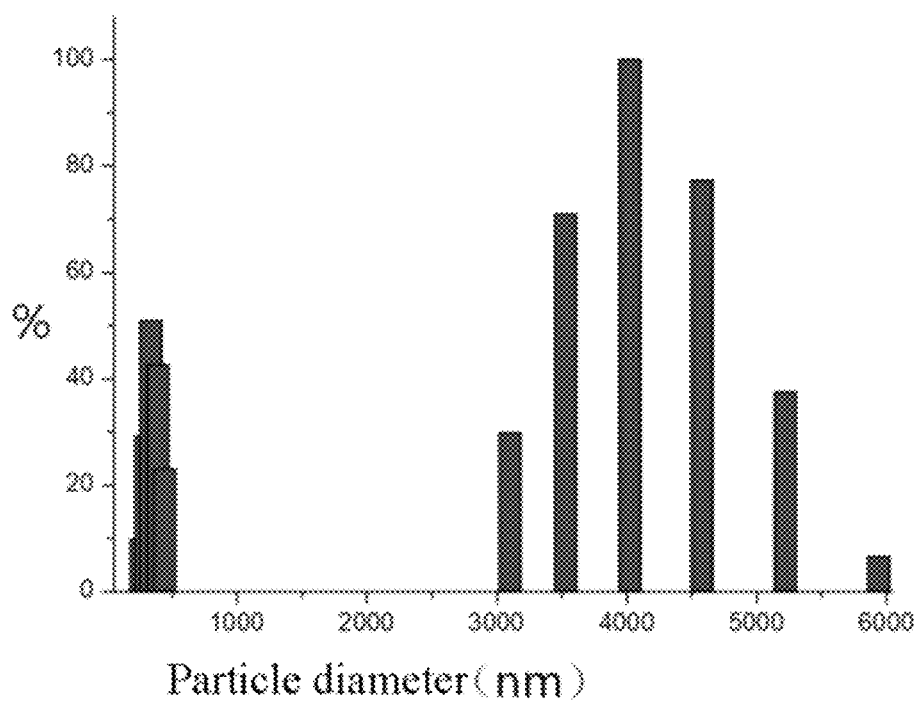
FIG. 4 is a DLS diagram showing particle diameter distribution of the telluride-modified sericin particles prepared in Example 3 after the telluride-modified sericin particles have been soaked in a 200 M of $H_2O_2$ solution for 24 hours.

In addition, particle diameters of the telluride-modified sericin protein particles prepared in Example 3 were measured by dynamic light scattering. As shown in FIGS. 1-3, the particle diameters were in a range of 580-1580 nm, and an average particle diameter of the particles was 1000 nm. FIG. 4 shows a DLS diagram showing particle diameter distribution of the sericin protein particles after the sericin protein particles were soaked in 200 M of $H_2O_2$ solution for 24 h; and the particle diameters of the sericin protein particles increased to a range of 3000-6000 nm, and an average particle diameter thereof was 4000 nm. In the presence of $H_2O_2$, the sericin protein particles with an oxidative stress property underwent depolymerization, and the particle diameters thereof became larger.

Example 4

1) 1.51 g of sodium borohydride and 4.84 g tellurium powder were added into 100 mL of water, and a resulting solution was heated to 80° C. under a condition of nitrogen protection to perform a reaction for 2.5 h to obtain a $Na_2Te_2$ aqueous solution. The $Na_2Te_2$ aqueous solution was cooled to room temperature, and 5.56 g of 10-bromo-dodecyl alcohol and 100 mL of tetrahydrofuran were added; and a resulting solution was heated to 50° C. to perform a reaction for 6 h. After the reaction was over, a resulting solution was cooled to room temperature, and a product was extracted by using dichloromethane. Then a dichloromethane phase was collected, and excess anhydrous magnesium sulfate was added for drying for 24 h; and a resulting solution was subjected to filtration and rotary evaporation to obtain a white solid powder of bis(1-hydroxydodecyl) telluride.

2) The obtained white solid powder of bis(1-hydroxydodecyl) telluride was dissolved in N,N-dimethylformamide to prepare a telluride solution having a mass concentration of 2%.

3) Sericin protein having a molecular weight of 50 KDa was dissolved in deionized water to prepare an aqueous solution of sericin protein with a mass concentration of 2%.

4) The telluride solution prepared in step 2) and the solution of the sericin protein prepared in step 3) were mixed at a volume ratio of 1:1, and a resulting solution was agitated for 8 h at 40° C. at a revolving speed of 500 rpm. Then, the solution was added dropwise into absolute ethanol to obtain a white precipitate. The precipitate was separated by centrifugation, and the obtained precipitate was telluride-modified sericin protein.

5) An aqueous solution of the telluride-modified sericin protein and an aqueous solution of magnesium chloride were prepared respectively, and the two solutions were mixed uniformly to obtain a mixed solution, in which a mass percentage concentration of the sericin protein was 2%, and a concentration of magnesium ions was 15 mmol/L. After a system of the solution was adjusted with HCl and NaOH to have a pH value of 8.0, the solution was placed into a thermostat at a temperature of 50° C. to perform a reaction, during which the solution was agitated continuously for 20 h at a resolving speed of 300 rpm. Resulting precipitate was separated by centrifugation. The obtained precipitate was sericin protein particles with an oxidative stress property. An average diameter of the sericin protein particles was 600 nm.

The above examples are only some embodiments of the present disclosure, and the protection scope of the present disclosure is not limited to the above examples; and the above examples do not represent all technical solutions under the inventive concept of the present disclosure. It shall be noted that, for those skilled in the art, additions and changes (for example, non-substantive modifications made to a concentration of sericin protein, a concentration of magnesium ions, a pH value, a temperature, a time length for a reaction and so on) may be made under the inspiration of the inventive concept of the present disclosure and specific examples without departing from the principles of the present disclosure, and these improvements and modifications shall also be considered as being within the protection scope of the present disclosure.

The invention claimed is:

1. A method for preparing sericin protein particles with an oxidative stress property, wherein the method comprises following steps:
   1) adding sodium borohydride and tellurium powder into water, heating to a temperature suitable for a reaction under nitrogen protection in order to obtain a $Na_2Te_2$ aqueous solution; cooling the $Na_2Te_2$ aqueous solution to room temperature, adding 10-bromo-dodecyl alcohol and an organic solvent thereto, and heating to a temperature suitable for a reaction; and then performing post-treatment in order to obtain a white solid powder of bis(1-hydroxydodecyl) telluride;
   2) preparing a telluride solution of the white solid powder of bis(1-hydroxydodecyl) telluride;
   3) uniformly mixing the telluride solution prepared in step 2) with a solution of sericin protein, and adding a resulting solution dropwise into absolute ethanol for a reaction in order to obtain a white precipitate of telluride-modified sericin protein; and
   4) preparing two solutions, wherein the two solutions are an aqueous solution of the telluride-modified sericin protein and an aqueous solution of magnesium ions; uniformly mixing the two solutions in order to obtain a mixed solution; adjusting the mixed solution with HCl and NaOH to have a pH value of 5.0-8.0 in order to obtain a pH-adjusted mixed solution; heating the pH-adjusted mixed solution to a temperature suitable for a reaction under a condition of agitating in order to obtain a resulting precipitate; and then separating the resulting precipitate in order to obtain sericin protein particles with an oxidative stress property.

2. The method for preparing a sericin protein particle with an oxidative stress property according to claim 1, wherein a molecular weight distribution of the sericin protein is 5-50 KDa.

3. The method for preparing a sericin protein particle with an oxidative stress property according to claim 1, wherein in step 4), after the aqueous solution of the telluride-modified sericin protein and the aqueous solution of the magnesium ions are mixed, a mass percentage concentration of the sericin protein is 0.05-2%, and a concentration of the magnesium ions is 5-15 mmol/L.

4. The method for preparing a sericin protein particle with an oxidative stress property according to claim 1, wherein the magnesium ions in step 4) are selected from any of magnesium chloride, magnesium nitrate, and magnesium sulfate.

* * * * *